(12) United States Patent
Salvadori

(10) Patent No.: US 8,292,859 B2
(45) Date of Patent: Oct. 23, 2012

(54) DRAINAGE DEVICE

(75) Inventor: Lawrence A. Salvadori, San Diego, CA (US)

(73) Assignee: Tyco Healthcare Group LP, Mansfield, MA (US)

( * ) Notice: Subject to any disclaimer, the term of this patent is extended or adjusted under 35 U.S.C. 154(b) by 399 days.

(21) Appl. No.: 12/119,211

(22) Filed: May 12, 2008

(65) Prior Publication Data

US 2009/0281527 A1    Nov. 12, 2009

(51) Int. Cl.
*A61M 1/00* (2006.01)
(52) U.S. Cl. ......... 604/327; 604/328; 604/317; 604/544
(58) Field of Classification Search .......... 604/327–330, 604/332, 346–347, 349
See application file for complete search history.

(56) References Cited

U.S. PATENT DOCUMENTS

| 3,593,765 | A | | 7/1971 | Monestere, Jr. | |
|---|---|---|---|---|---|
| D221,911 | S | * | 9/1971 | Ericson | D24/118 |
| 3,901,235 | A | * | 8/1975 | Patel et al. | 604/323 |
| 4,265,243 | A | | 5/1981 | Taylor | |
| 4,343,316 | A | * | 8/1982 | Jespersen | 600/584 |
| 4,417,892 | A | | 11/1983 | Meisch | |
| 4,443,219 | A | * | 4/1984 | Meisch et al. | 604/323 |
| 4,460,362 | A | * | 7/1984 | Bates | 604/323 |
| 4,462,510 | A | | 7/1984 | Steer et al. | |
| 4,529,398 | A | | 7/1985 | Wong et al. | |
| 4,592,750 | A | * | 6/1986 | Kay | 604/337 |
| 4,693,712 | A | | 9/1987 | Bates | |
| 4,712,567 | A | * | 12/1987 | Gille et al. | 600/584 |
| 4,936,837 | A | * | 6/1990 | Wexler et al. | 604/326 |
| 5,026,359 | A | | 6/1991 | Burroughs | |
| 5,176,665 | A | | 1/1993 | Watanabe et al. | |
| 5,217,443 | A | | 6/1993 | Oxley | |
| 5,279,601 | A | | 1/1994 | Lichte | |
| 5,406,650 | A | * | 4/1995 | Einbinder | 4/144.2 |
| 5,417,676 | A | | 5/1995 | Watanabe et al. | |
| 5,489,281 | A | | 2/1996 | Watanabe et al. | |
| 5,496,299 | A | * | 3/1996 | Felix et al. | 604/319 |
| 5,919,146 | A | | 7/1999 | Propp | |
| 6,132,407 | A | | 10/2000 | Genese et al. | |
| 6,261,254 | B1 | * | 7/2001 | Baron et al. | 604/323 |
| 6,652,495 | B1 | | 11/2003 | Walker | |
| 2003/0032944 | A1 | | 2/2003 | Cawood | |
| 2006/0189962 | A1 | | 8/2006 | Burtoft | |
| 2007/0149934 | A1 | | 6/2007 | Christensen | |

* cited by examiner

*Primary Examiner* — Michele M Kidwell
(74) *Attorney, Agent, or Firm* — Lisa E. Winsor, Esq.

(57) ABSTRACT

A urine collection system includes a collection element configured for operable connection to a catheter for accumulating urine expelled from a subject and defining an opening for passage of the urine from the collection element and a drainage device extending from the collection element and positioned about the opening in the collection element. The drainage device includes a drain spout defining an outlet port disposed above the opening in the collection element. Urine collected in the collection element exits the opening within the collection element to be drained through the outlet port of the drain spout until the volume of urine reaches a predetermined level below the outlet port. Upon reaching the predetermined level, the urine remaining within the drainage device establishes a fluid trap substantially preventing contaminants from entering the collection element through the opening.

9 Claims, 4 Drawing Sheets

# DRAINAGE DEVICE

BACKGROUND

1. Technical Field

The present disclosure relates to urine collection systems. More particularly, the present disclosure relates to a drainage device for a urine collection system.

2. Background of Related Art

Urine collection systems are known and are commonly used to collect urine from a catheterized patient. Whenever a patient is catheterized, it is important for the collection system to remain "closed" to the greatest degree possible to minimize and/or to prevent urinary tract infections from occurring. Bacterial invasions may occur at the junction of the catheter and meatus, at the disconnection point of the catheter and collection system, at any open sampling site, and/or at the open drain site used to routinely drain the system of fluid.

Traditional urine collection systems used for in-dwelling catheterization incorporate a flexible collection bag with an ordinary drain device. Generally, the drain device is affixed to the bottom of the bag and consists of a valve or tube with a clamp. When opened, the valve completely drains the fluid from the bag. In this manner, when the fluid is completely drained from the bag, an opening or passage is created between the inside of the bag and the environment. This opening can provide a passageway for air-borne contaminates to enter the urine collection system and initiate bacterial growth that could result in an infection to the patient.

Therefore, it would be beneficial to have a drain device that prevents the "opening" of the urine collection system to contaminates.

SUMMARY

Accordingly, the present disclosure is directed to a urine collection system including a collection element configured for operable connection to a catheter for accumulating urine expelled from a subject and defining an opening for passage of the urine from the collection element and a drainage device extending from the collection element and positioned about the opening in the collection element. The drainage device includes a drain spout defining an outlet port disposed above the opening in the collection element. Urine collected in the collection element exits the opening within the collection element to be drained through the outlet port of the drain spout until the volume of urine reaches a predetermined level below the outlet port. Upon reaching the predetermined level, the urine remaining within the drainage device establishes a fluid trap substantially preventing contaminants from entering the collection element through the opening.

The drainage device may be selectively engageable with the collection bag. The drainage device may be integrally formed with the collection bag. The drainage device may include an anti-microbial pellet, the antimicrobial pellet disposed within the volume of urine forming the fluid trap. The drainage device optionally may include a cover selectively engageable with the drain spout. The drain spout may be configured for operable engagement with a hose. In one embodiment, the drain spout includes a valve having a closed condition to prevent flow of fluids from the drain spout. The valve may be manipulated by the user to assume an open condition.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
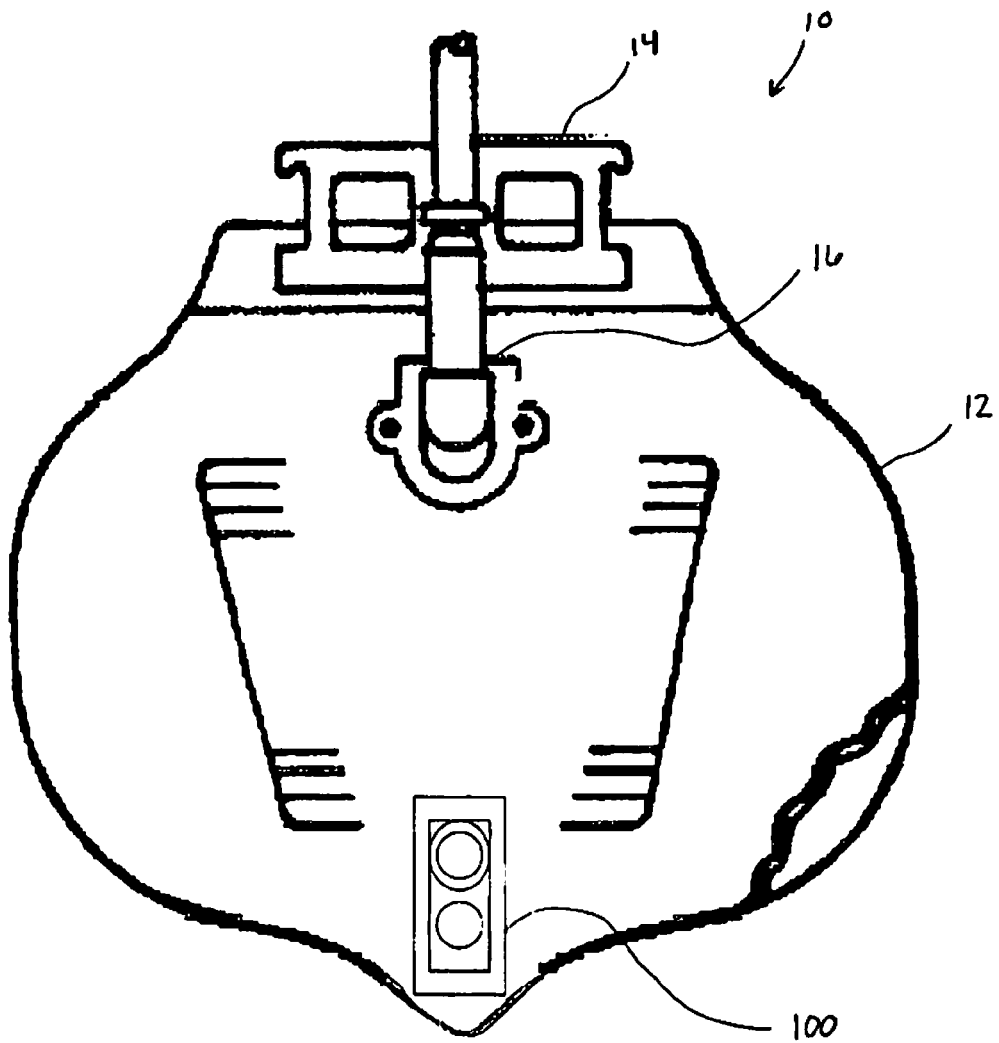
FIG. 1 is a urine collection system according to the present disclosure.
Figure 2C:
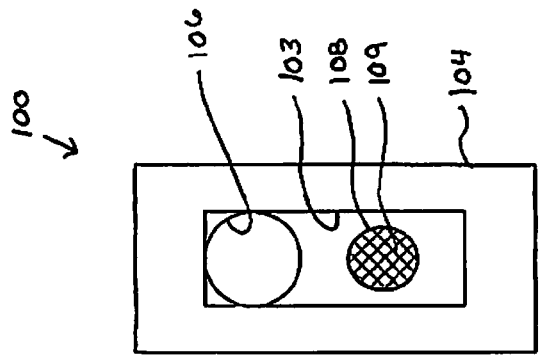
FIGS. 2B and 2C are respective front and rear views of the drainage device of FIG. 2A.
Figure 2D:
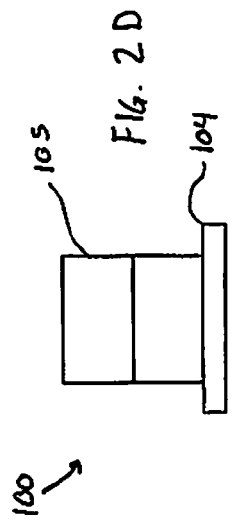
FIGS. 2D and 2E are respective top and bottom views of the drainage device of FIGS. 2A-2C.
Figure 2A:
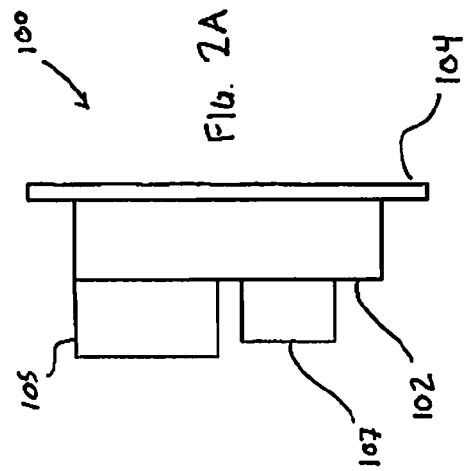
FIG. 2A is a side view of a drainage device of the urine collection system of FIG. 1.
Figure 2E:
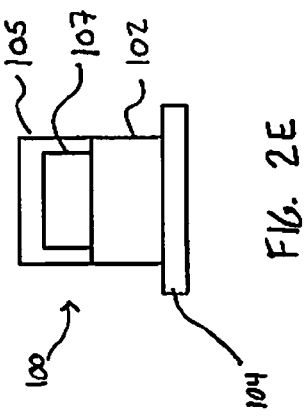
Figure 2B:
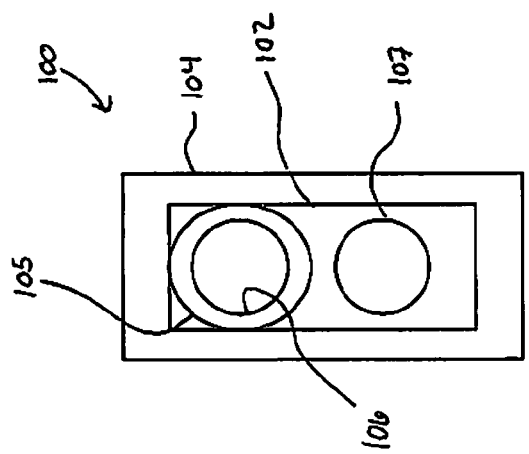

Referring initially to FIG. 1, a urine collection system according to the present disclosure is shown generally as urine collection system 10. Urine collection system 10 includes a collection bag 12, a hanger 14 for supporting collection bag 12, a connection means 16 for connecting collection bag 12 to a catheter (not shown) and a drainage device 100 for draining collection bag 12. As will become apparent from the following discussion, drainage device 100 may be adapted for use with other urine collection and or other fluid collection systems such as blood or other bodily fluids. Therefore, the aspects of the present disclosure should not be read as limited to urine collection system 10.

Turning now to FIGS. 2A-2E, in conjunction with FIG. 3, drainage device 100 defines a housing 102 having a generally rectangular shape; however, alternate configurations are envisioned, including circular or triangular housings. As will be discussed in further detail below, housing 102 defines a cavity 103 for receiving fluid from collection bag 12 (FIG. 1). Drainage device 100 includes a flange 104 extending about a perimeter of housing 102. Flange 104 is configured for securing drainage device 100 to collection bag 12 (FIG. 1). Drainage device 100 may be secured to collection bag 12 using adhesive, bonding, mechanical fasteners or other suitable methods. It is envisioned that drainage device 100 may be selectively engageable, i.e. removable, with collection bag 12. In an alternate embodiment, drainage device 100 may be integrally formed with collection bag 12.

Drainage device 100 includes a drain spout 105 extending from housing 102. Drain spout 105 defines an outlet 106 in fluid communication with cavity 103. Drain spout 105 may be configured for operable engagement with a tube or hose (not shown) to permit drainage of collection bag 12 (FIG. 1) into a waste disposal vessel or intermediary container. Drain spout 105 may further be configured to include a cap or lid 110 (FIG. 3A) to retain fluid "F" in collection bag 12. In an alternate embodiment, drain spout 105 may instead include a valve (not shown) for retaining fluid "F" with urine collection system 10.

Drainage device 100 further includes an extension 107 extending from housing 102. Extension 107 defines a recess 108 configured for receiving an anti-microbial pellet 109 (FIG. 3). As will be discussed below, extension 107 is located such that anti-microbial pellet 109 is submersed in fluid "F" that remains in urine collection system 10 after collection bag 12 has been drained using drainage device 100. Anti-microbial pellet 109 may include any suitable anti-microbial agent, including materials capable of releasing silver ions, desiccants or the like.

The operation of urine collection system 10, and more particularly drainage device 100 will be described with reference to FIGS. 3A and 3B. As discussed above, drainage device 100 may be securely attached, removable engaged or integrally formed with collection bag 12. Drainage device 100 is positioned on a lower portion of collection bag 12 about an opening 12a. Drainage device 100 is oriented such that drain spout 105 is located above opening 12a formed in collection bag 12. As shown, when drainage device 100 is securely attached and/or integrally formed with collection bag 12, drain spout 105 requires a cover 110 or valve 111 to prevent collection bag 12 from draining as fluid "F" enters urine collection system 10. Valve 111 may be any suitable zero-closure valve, e.g., a duck bill valve, which is closed in a normal condition but may open in response to the pressure of fluids within the cavity 103. FIG. 3B illustrates an alternate cover or valve 113 which pivots, e.g., about pivot pin 115, in the direction of directional arrows "k" between the closed position depicted in FIG. 3B and the open position depicted in phantom. Valve 113 may be selectively manually movable between the open and closed positions.

Cover 110 is selectively engageable with drain spout 105 using threaded engagement, friction fit or other suitable method. When drainage device 100 is selectively engageable with collection bag 12, a cover 110 may not be necessary to selectively retain fluid "F" within collection bag 12. Instead, collection bag 12 may be configured such that opening 12a in collection bag 12 remains sealed until drainage device 100 is properly position on collection bag 12, or opening 12a becomes unsealed as drainage device 100 is secured to collection bag 12.

Figure 3A:
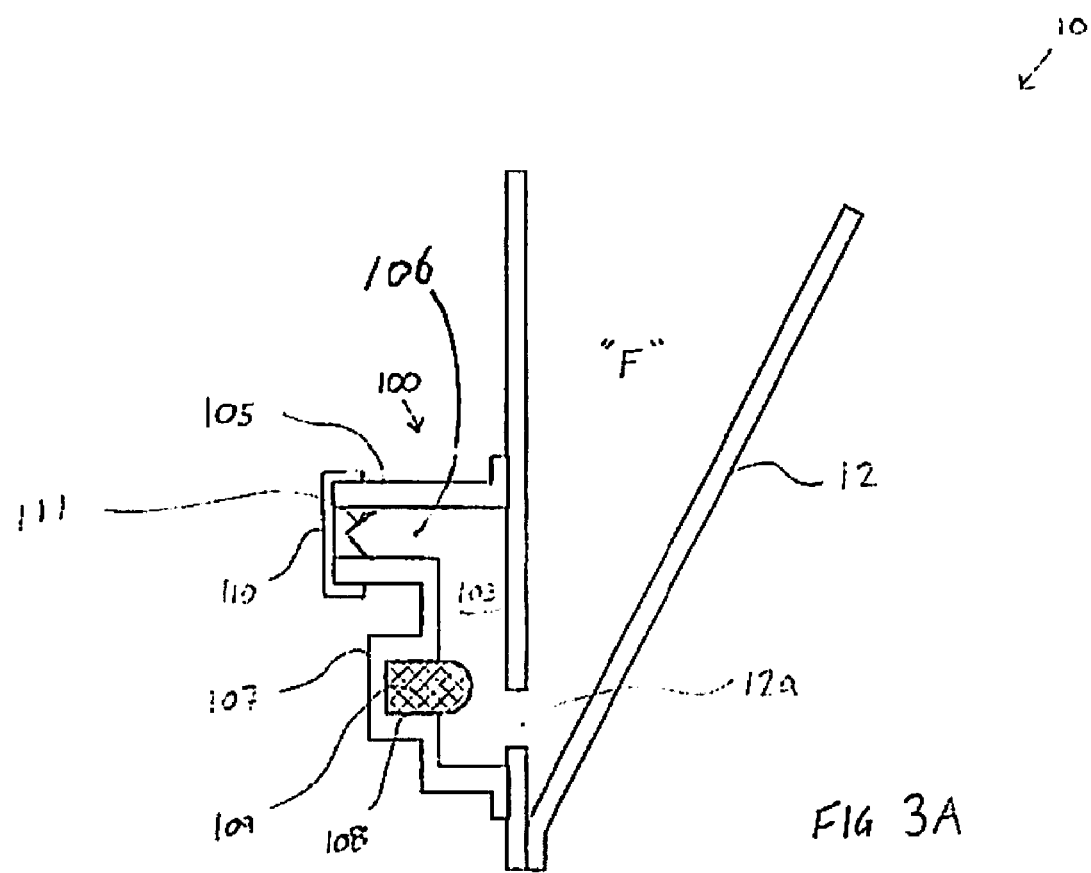
FIGS. 3A and 3B are cross-sectional side views of the urine collection system of FIG. 1.
Figure 3B:
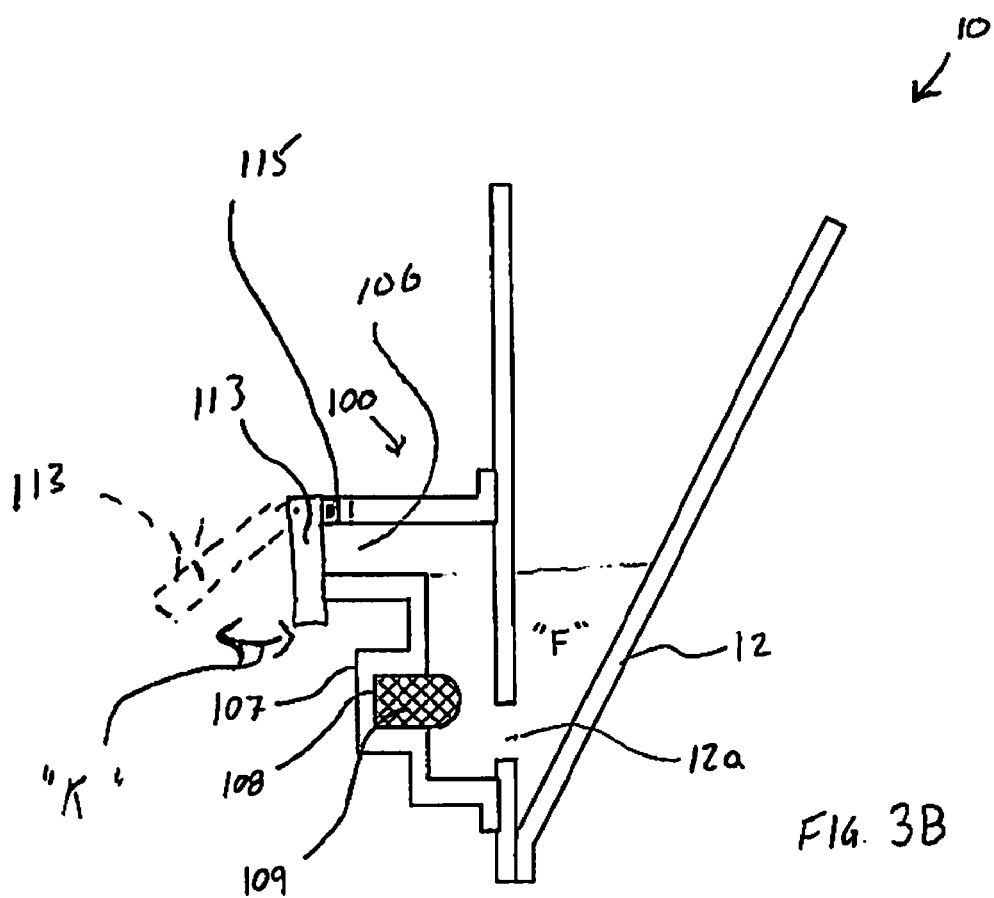

Referring initially to FIG. 3A, drainage device 100 includes cover 110 and/or optionally valve 113 to prevent the flow of fluid "F" out of drain spout 105 once the level of fluid "F" within collection bag 12 passes the bottom of outlet 106. While cover 110 positioned over drain spout 105, collection bag 12 fills with fluid "F". Removal of cover 110 causes the flow of fluid "F" from collection bag 12, out opening 12a, into cavity 103 of housing 102, and out drain spout 105. Once the fluid level within collection bag 12 reaches the bottom of outlet 106, fluid "F" ceases to flow out of drain spout 105. The remaining fluid "F" in urine collection system 10 forms a trap or airlock that prevents outside air, and thus, contaminates, from entering collection bag 12. Anti-microbial pellet 109 renders any contaminates in the remaining fluid "F" harmless. Drain spout 105 may be recovered with cover 110 such that urine collection system 10 may continue to be used to collect fluid "F". The draining of urine collection system 10 may be repeated as described above as necessary.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:
1. A urine collection system comprising:
a collection element configured for operable connection to a catheter for accumulating urine expelled from a subject, the collection element defining an opening for passage of the urine from the collection element; and
a drainage device extending from the collection element and positioned about the opening in the collection element, the drainage device including a drain spout defining an outlet port fixedly disposed above the opening in the collection element, the drain spout being secured to the collection element such that the outlet port remains above the opening in the collection element during urine drainage;
whereby urine collected in the collection element exits the opening within the collection element to be drained through the outlet port of the drain spout until the volume of urine reaches a predetermined level below the outlet port and wherein upon reaching the predetermined level, the urine remaining within the drainage device establishes a fluid trap substantially preventing contaminants from entering the collection element through the opening.

2. A urine collection system according to claim 1, wherein the drainage device is selectively engageable with the collection bag.

3. A urine collection system according to claim 1, wherein the drainage device is integrally formed with the collection bag.

4. A urine collection system according to claim 1, wherein the drainage device includes an anti-microbial pellet, the antimicrobial pellet disposed within the volume of urine forming the fluid trap.

5. A urine collection system according to claim 1, wherein the drainage device includes a cover selectively engageable with the drain spout.

6. A urine collection system according to claim 1, wherein the drain spout is configured for operable engagement with a hose.

7. A urine collection system according to claim 1, wherein the drain spout includes a valve having a closed condition to prevent flow of fluids from the drain spout.

8. A urine collection system comprising:
a collection element configured for operable connection to a catheter for accumulating urine expelled from a subject, the collection element defining an opening for passage of the urine from the collection element; and
a drainage device defining a cavity, the draining device being secured to an external surface of the collection element such that the opening communicates with the cavity, the drainage device including a drain spout defining an outlet port which is fixedly disposed above the opening in the collection element, the drain spout remaining above the opening in the collection element during urine drainage;
whereby urine collected in the collection element flows from the opening within the collection element into the cavity until the volume of urine within the collection element reaches a predetermined level below the outlet port and wherein upon reaching the predetermined level, urine remaining within the cavity of the drainage device establishes a fluid trap between the outlet port and the opening substantially preventing contaminants from entering the collection element through the opening.

9. A urine collection system comprising:
a collection element configured for operable connection to a catheter for accumulating urine expelled from a subject, the collection element defining an opening for passage of the urine from the collection element; and
a drainage device including a housing fixedly secured to the collection element about the opening, the housing defining an interior cavity communicating with the opening and defining an outlet port positioned in a fixed relation relative to the opening at a position above the opening, the outlet port remaining above the opening the collection element during urine drainage.

* * * * *